United States Patent [19]

Fuller

[11] 4,047,892
[45] Sept. 13, 1977

[54] LIQUID CHROMATOGRAPHIC ANALYSIS FOR STYRENE-BUTADIENE MONOMERS

[75] Inventor: Edward N. Fuller, Bartlesville, Okla.
[73] Assignee: Phillips Petroleum Company, Bartlesville, Okla.
[21] Appl. No.: 701,727
[22] Filed: July 1, 1976
[51] Int. Cl.² .......................................... G01N 31/08
[52] U.S. Cl. ................................ 23/232 C; 73/61.1 C
[58] Field of Search ................... 23/232 C; 210/31 C; 73/61.1 C

[56] References Cited

U.S. PATENT DOCUMENTS 3,292,420  12/1966  Scott .............................. 23/232 C X
3,549,524  12/1970  Haller ........................... 73/61.1 C X

OTHER PUBLICATIONS

Chem. & Eng. News, Oct. 29, 1973, p. 22.

*Primary Examiner*—Robert M. Reese

[57] ABSTRACT

An improved method for the separation of the individual components contained in a process stream consisting essentially of 1,3-butadiene, styrene and cyclohexane is provided which comprises passing a sample of the stream through a silica-filled column in a liquid chromatographic apparatus. The carrier is passed through a drying chamber prior to introducing the carrier onto the column.

5 Claims, 3 Drawing Figures

LIQUID CHROMATOGRAPHIC ANALYSIS FOR STYRENE-BUTADIENE MONOMERS

This invention relates to liquid chromatography. In one aspect this invention relates to a method for analyzing a liquid mixture of polymerizable monomers and a solvent by liquid chromatography.

BACKGROUND OF THE INVENTION

Process liquid chromatography (PLC) is increasingly being used in the chemical industries to extend the analysis capabilities of process gas chromatography (PGC). In many respects, PLC can be considered as a complement to PGC. There is considerable overlap between the two chromatographic techniques since many compounds can either be vaporized or dissolved. Many PLC analyses are involved with complex separations involving compounds that are difficult or impossible to separate by PGC. These include analyses of compounds that are non-volatile, thermally unstable, high boiling and which require excessive temperatures to vaporize, or which polymerize or react on heating.

One analysis of potential commercial importance is that of the mixture of 1,3-butadiene, styrene and cyclohexane. Such an analysis would be of some importance in the monitoring of operations in SBR rubber production. However, this analysis has been difficult to carry out in the past by gas chromatography due to the tendency of the styrene to polymerize on the column. This analysis has also been difficult to carry out by liquid chromatography due to incomplete separation of the 1,3-butadiene and the cyclohexane.

SUMMARY OF THE INVENTION

Accordingly, it is an object of this invention to provide an improved process for the analysis of a mixture of 1,3-butadiene, styrene and cyclohexane.

Other objects, aspects and advantages of this invention will be readily apparent to those skilled in the art from the reading of the following disclosure.

In accordance with the present invention there is provided an improved process for analyzing a process stream consisting essentially of a mixture of 1,3-butadiene, styrene and cyclohexane by liquid chromatography which provides complete separation of the 1,3-butadiene and the cyclohexane. The process of this invention comprises introducing a sample of such mixture into a chromatographic column containing a partitioning material that selectively retards passage therethrough of the components of the mixture, introducing a carrier fluid into the column at a predetermined flow rate to carry the mixture through the column to effect separation of the mixture into its components, and separately determining the quantity of each component, wherein the carrier fluid is dried by passing same through a drying column prior to being introduced into the partitioning column.

DETAILED DESCRIPTION

The process of this invention is of particular applicability in process monitoring and control of a solution polymerization process for preparing copolymers of 1,3-butadiene and styrene, such as the process disclosed in Zelinski, U.S. Pat. No. 2,975,160, issued Mar. 14, 1961, the disclosure of which is incorporated herein by reference.

Generally, the mixture to be analyzed will contain 1,3-butadiene and styrene in a weight ratio in the range of 5:95 to 95:5, together with about 250 to 1000 parts by weight of cyclohexane per 100 parts by weight of the above monomer mixture.

Figure 1:
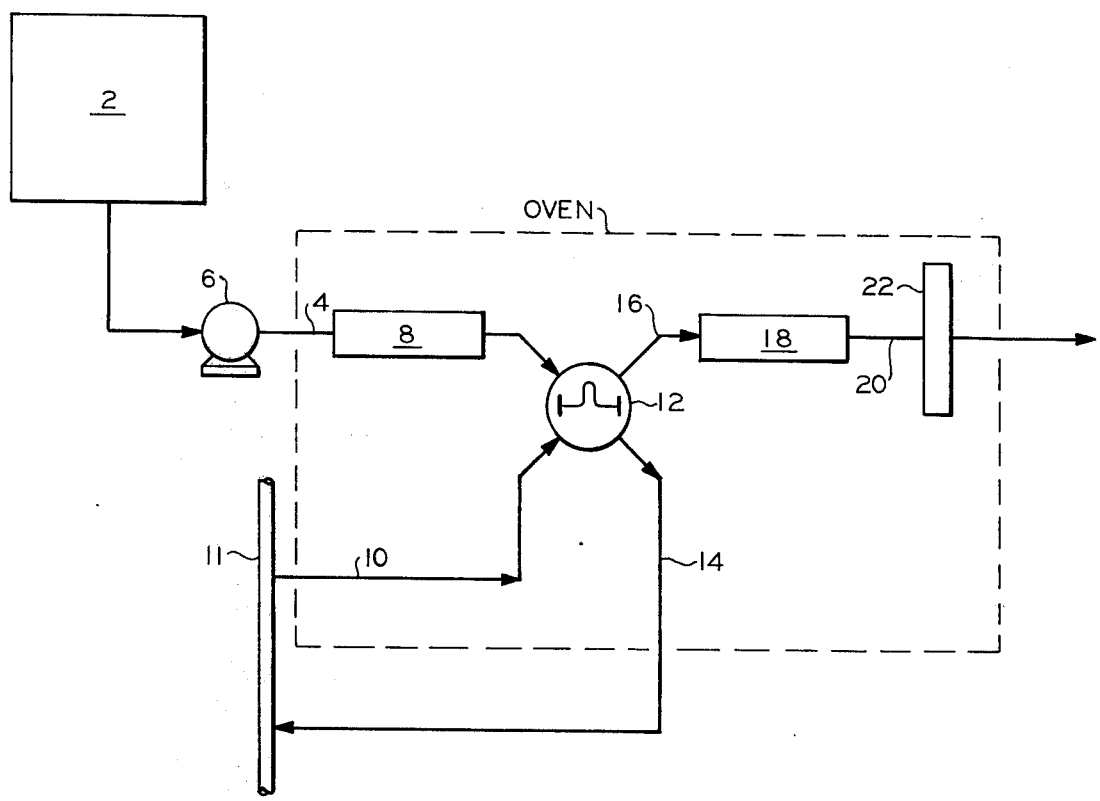
FIG. 1 is a shematic representation of a liquid chromatographic system of this invention.

Referring now to the drawings, FIG. 1 shows a carrier supply tank 2 for storing the carrier fluid. The carrier fluid is passed through line 4 by means of pump 6 to drying chamber 8 wherein the carrier fluid is contacted with a drying agent such as for example, molecular sieves. Sample supply from a process stream 11 is introduced via line 10 to sample valve 12. This sample stream can be taken off continuously and returned to the process stream 11 via line 14 except during the period when it is desired to analyze the sample stream. At this point, sample valve 12 is switched so as to trap a small portion of the stream flowing therethrough and introduce same into line 16 along with the carrier fluid. The sample is then carried by means of the carrier fluid vai line 16 to chromatographic column 18 wherein the sample mixture is separated into its individual components. Coming out of column 18 is line 20 which carries the eluted portions of the sample to detector 22.

Many conventional parts such as temperature controllers, preheaters, pulse damping means, pressure monitors, valves and the like have been omitted from the system for the sake of simplicity but their inclusion is understood by those skilled in the art.

The drying chamber 8 is packed with molecular sieves having a nominal pore diameter of about 10 Angstroms. The drying chamber is dry packed and, preferably, is baked out at about 250° C while purging with an inert gas, such as helium, for about 12 hours.

The column 18 is packed with an alumina or silica gel partitioning material having a particle size in the approximate range of 2 to 40 microns, preferably 15 to 37 microns, and a surface area in the approximate range of 250 to 450, preferably about 300, square meters per gram. A suitable packing material is Porasil T, available from Waters Associates, Farmington, Mass., a porous silica having a particle size of 15-25 microns.

The column 18 is dry packed and is activated at a temperature in the range of 150° to 250° C while purging with an inert gas, such as helium, for several hours. It is presently preferred that such activation be carried out at about 150° C.

The carrier fluid can be any carrier fluid of suitable low polarity known in the art, e.g., n-hexane, n-pentane or isopentane. In a presently preferred embodiment the carrier fluid is n-hexane.

The following example illustrates the invention:

EXAMPLE

A 10 microliter sample of a mixture of cyclohexane, 1,3-butadiene and styrene, typical of a polymerizable mixture, was passed to a liquid chromanalyzer via a high pressure sampling valve such as is shown in FIG. 1. n-Hexane was used as the carrier fluid. The chromatographic column was 5 feet long, 50 -inch diameter tubing packed with Porasil T, having a particle size in the range of 15 to 25 microns. The carrier pressure was 1000 psig. The components were detected by a refractive index detector.

Figure 2:
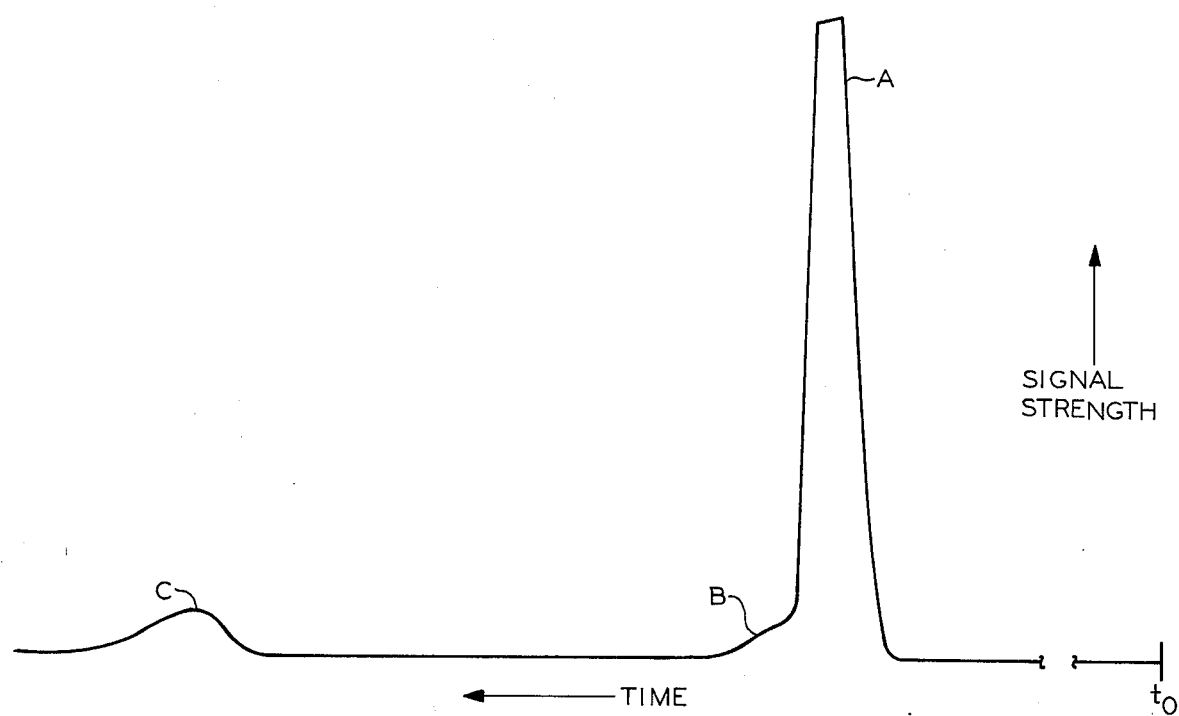
FIG. 2 is a curve showing a typical separation not utilizing the invention.
Figure 3:
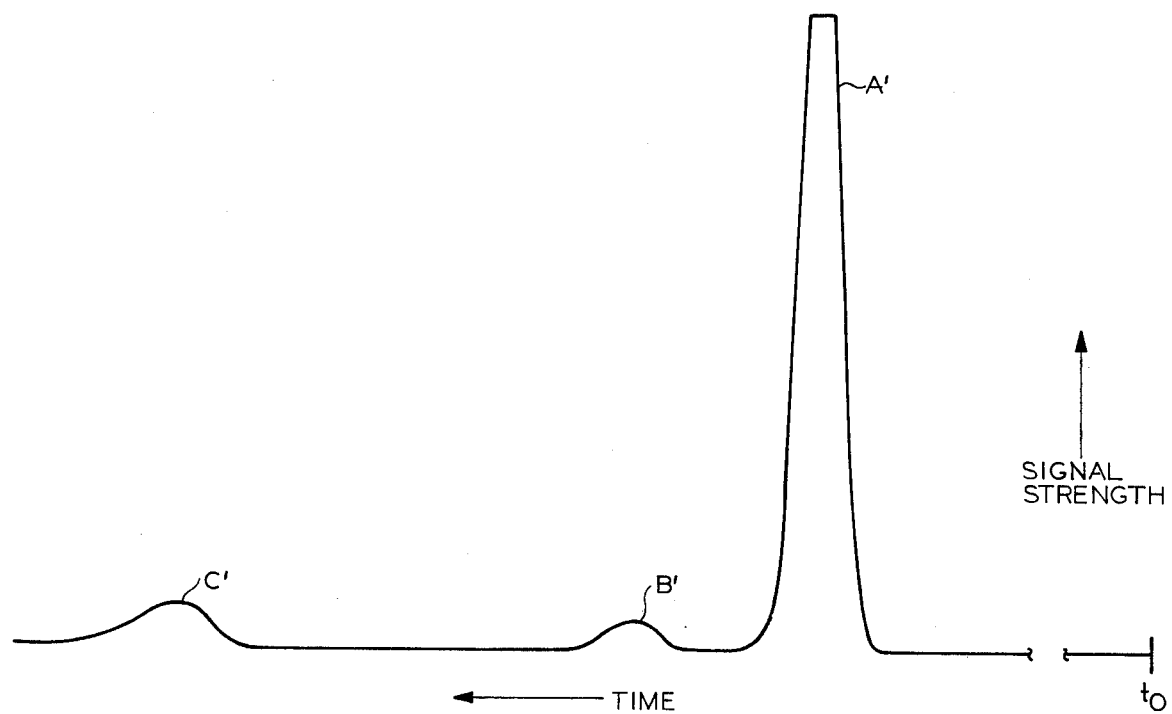
FIG. 3 is a curve showing a typical separation utilizing the invention.

The first materials to come through the column were cyclohexane, labeled peak A in FIG. 2, and 1,3-butadiene, labeled peak B. Thereafter, the styrene, labeled peak C, came through. The 1,3-butadiene peak, B, is incompletely separated from the cyclohexane peak, A.

A second analysis was performed as before but a drying chamber was inserted between the high pressure pump and the high pressure sampling valve 12 as shown in FIG. 1. The guard chamber was 2 feet long by ¼-inch tubing packed with Type 13X molecular sieves having a nominal pore diameter of 10 Angstroms, in 60/80 mesh powder form. A 10 microliter sample of the mixture was passed onto the column, as above. The first material to come through the column was cyclohexane, labeled A' in FIG. 3, followed by 1,3-butadiene, labeled B' and styrene, labeled C'.

It is readily apparent from a comparison of FIGS. 2 and 3 that, by pretreating of the n-hexane carrier in accordance with the invention, resolution of the 1,3-butadiene peak is greatly improved.

Reasonable variations and modifications, which will be apparent to those skilled in the art, can be made in this invention without departing from the spirit and scope thereof.

What is claimed is:

1. A process for the liquid chromatographic analysis of a mixture of styrene, 1,3-butadiene and cyclohexane which comprises:
   introducing a sample of said mixture into a chromatographic column having a partitioning material therein which selectively retards passage therethrough of the components of said mixture, drying a carrier fluid by passing same through a drying chamber and thereafter introducing the thus-dried carrier fluid into said column at a predetermined flow rate to carry said mixture through said column to effect separation of said mixture into said styrene, said 1,3-butadiene and said cyclohexane, and thereafter separately determining the quantity of styrene, 1,3-butadiene and cyclohexane.

2. The process of claim 1 wherein said partitioning material is a silica gel having a surface area in the approximate range of 250–450 square meters per gram and a particle size in the approximate range of 2 to 40 microns.

3. The process of claim 1 wherein said partitioning material is a silica gel having a surface area of about 300 square meters per gram and a particle size of about 15 to 37 microns.

4. The process of claim 1 wherein said carrier is dried by passing same through a bed of molecular sieves having a nominal pore diameter of about 10 angstroms.

5. The process of claim 1 wherein said carrier fluid is n-hexane.

* * * * *